(12) United States Patent
Sasaki et al.

(10) Patent No.: US 6,180,094 B1
(45) Date of Patent: Jan. 30, 2001

(54) REMEDIES FOR HYPERPHOSPHATEMIA

(75) Inventors: Yoshiyuki Sasaki; Yutaka Ishii, both of Saitama (JP)

(73) Assignee: Nikken Chemicals Co., Ltd., Tokyo (JP)

(*) Notice: Under 35 U.S.C. 154(b), the term of this patent shall be extended for 0 days.

(21) Appl. No.: 09/147,534

(22) PCT Filed: Jul. 17, 1997

(86) PCT No.: PCT/JP97/02486

§ 371 Date: Jan. 15, 1999

§ 102(e) Date: Jan. 15, 1999

(87) PCT Pub. No.: WO98/03185

PCT Pub. Date: Jan. 29, 1998

(30) Foreign Application Priority Data

Jul. 19, 1996 (JP) ........................................ 207574
Jan. 31, 1997 (JP) ........................................ 031461

(51) Int. Cl.[7] ................................................ A61K 31/785
(52) U.S. Cl. ...................................... 424/78.12; 514/814
(58) Field of Search ................................ 424/78.1, 78.12

(56) References Cited

U.S. PATENT DOCUMENTS 5,114,709 * 5/1992 St. Pierre et al. ................ 424/78.12
5,487,888 * 1/1996 Mandeville, III et al. ......... 424/78.1
5,496,545   3/1996 Holmes-Earley et al. .
5,980,881 * 11/1999 Mitsuka et al. ................... 424/78.1

FOREIGN PATENT DOCUMENTS

94/27621  12/1994 (WO).
95/05184   2/1995 (WO).

OTHER PUBLICATIONS

Thomas et al. "Inhibition of Iron Absorption by Cholestyramine", Digestive Diseases, vol. 17, No. 3, pp. 263–269, 1972.

Clinical Research, vol. 18, p. 38, 1970.

Bursaux et al., "Oxygen Transport in Children on Maintenance Haemodialysis", Clin. Sci. Mol. Med., vol. 54, No. 1, pp. 85–91, 1978.

Brown et al., "Design of Iron (III) Chelates in Oral Treatment of Anemia: Solution Properties and Absorption of Iron(III) Acetohydroxamate in Anemic Rats", Bioinorg. Chem., 1978, vol. 9, No. 3, pp. 255–275.

* cited by examiner

Primary Examiner—Peter F. Kulkosky
(74) Attorney, Agent, or Firm—Greenblum & Bernstein, P.L.C.

(57) ABSTRACT

A medicament which comprises as an active ingredient a weakly basic anion exchange resin chelating with ferric ions, preferably a polyamine-type or an acrylic-type resin. The medicament has excellent adsorbability and selectivity to phosphate ions and efficiently adsorb phosphate ions in vivo, and accordingly, is useful for therapeutic and/or preventive treatment of hyperphosphatemia.

18 Claims, 1 Drawing Sheet

REMEDIES FOR HYPERPHOSPHATEMIA

TECHNICAL FIELD

The present invention relates to a medicament which comprises a weakly basic anion exchange resin chelating with ferric ions as an active ingredient. The medicament is useful as a medicament for therapeutic and/or preventive treatment of hyperphosphatemia.

BACKGROUND ART

Patients of chronic renal failure are unavoidably treated by dialysis normally at regular intervals over a prolonged period of time, and pathological conditions of increased plasma phosphate concentrations (4.5 mg/dl or more), i.e., hyperphosphatemia, are often appeared in the patients. Because no direct etiological treatment of hyperphosphatemia has been developed so far, diet therapy to lower phosphate absorption, or as a symptomatic therapy, treatment by oral administration of a medicament for hyperphosphatemia which adsorbs phosphate ions in the digestive tract are generally applied. As medicaments for therapeutic treatment of hyperphosphatemia, aluminum hydroxide gel and precipitated calcium carbonate are commonly used.

International Publication WO95/05184 discloses a method for eliminating phosphate ions in vivo by using a polymer such as polyallylamine, polyethylenimine or other, preferably a cross-linked polymer obtained by using a crosslinking agent such as epichlorohydrin or the like. The publicaition teaches that strongly basic anion exchange resins such as Dowex are not preferred from viewpoints that doses are inevitably high because of their weak adsorbability of phosphate ions and the resins may adsorb salts of bile acids. The publication also teaches that the aforementioned polymers are improved in these points compared to the conventional resins.

Aluminum hydroxide gel used as a medicament for therapeutic treatment of hyperphosphatemia has problems of high daily dosage, and moreover, bad taste, which cause difficulty in administration by a patient. Additionally, aluminum ions, formed by dissociation from the aluminum hydroxide gel in contact with gastric hydrochloric acid, are absorbed from the intestinal tract, and as a result, prolonged administration may sometimes cause precipitation of aluminum in the brain and bones and induces so-called osteopathic aluminosis or encephalopathic aluminosis, microcytic anemia or other. On the other hand, precipitated calcium carbonate used as a medicament for therapeutic treatment of hyperphosphatemia also has a problem that calcium ions formed by dissociation in contact with gastric hydrochloric acid may cause hypercalcemia.

In pathologic conditions of chronic renal failure accompanied by hyperphosphatemia, complications such as iron deficiency anemia, metabolic acidosis or other may often appear in patients. It is well known that administration of aluminum hydroxide gel under these conditions may further deteriorate the anemia. In addition, it is also known that cholestyramine (a preparation comprising a polystyrene-type strongly basic anion exchange resin: "Questran", Bristol Myers Squibb Co.), which is used as a cholesterol depressant that adsorbs bile acids, also adsorbs iron ions and suppresses the iron absorption from the intestinal tract to reduce the iron concentration in blood and tissues and lower the hematocrit level. which advances iron deficiency anemia (Digestive Diseases, Vol. 17, No. 3, p.263–269, 1972; and Clin. Res. Vol. 18, p.38, 1970). In addition, international Publication WO94/27621 discloses a method for binding iron ions by using a polymer having amino groups. Accordingly, if polystyrene resins and acrylic resins having amino groups, per se, are administered, the aforementioned adverse effect (iron deficiency anemia) may possibly be generated.

DISCLOSURE OF THE INVENTION

An object of the present invention is to provide a medicament useful for therapeutic and/or preventive treatment of hyperphosphatemia, and free from adverse effects. More specifically, the object is to provide a medicament for therapeutic and/or preventive treatment of hyperphosphatemia which has excellent phosphate eliminating ability and can selectively eliminate phosphate. In addition, another object of the present invention is to provide a method for therapeutic and/or preventive treatment of hyperphosphatemia.

The inventors of the present invention conducted various researches to achieve the foregoing objects. As a result, they found that weakly basic anion exchange resins chelating with ferric ions can efficiently adsorb phosphate ions in vivo, and when the resins were used as medicaments, no adverse effect such as osteopathic aluminosis, encephalopathic aluminosis, hypercalcemia, iron deficiency anemia or other were generated. The present invention was achieved on the basis of these findings.

The present invention thus provides a medicament which comprises a weakly basic anion exchange resin chelating with ferric ions as an active ingredient, preferably, it provides the aforementioned medicament used as a medicament for therapeutic and/or preventive treatment of hyperphosphatemia.

According to a preferred embodiment of the present invention, there is provided the aforementioned medicament which comprises a polyamine-type weakly basic anion exchange resin chelating with ferric ions as an active ingredient. According to another preferred embodiment, there is also provided the aforementioned medicament which comprises an acrylic-type weakly basic anion exchange resin chelating with ferric ions as an active ingredient.

These medicaments, preferably the medicaments for therapeutic and/or preventive treatment of hyperphosphatemia, are typically provided in the form of pharmaceutical compositions which comprise the aforementioned active ingredient together with pharmaceutically acceptable additives.

According to another aspect of the present invention, there is provided use of a weakly basic anion exchange resin chelating with ferric ions for the manufacture of the medicaments defined above, preferably a medicament for therapeutic and/or preventive treatment of hyperphosphatenia. According to preferred embodiment of the invention, there is provided the aforementioned use wherein the weakly basic anion exchange resin is a polyamine-type or an acrylic-type resin.

According to further aspect of the present invention, there is provided a method for therapeutic and/or preventive treatment of hyperphosphatemia which comprises the step of administering to a patient a therapeutically and/or preventively effective amount of a weakly basic anion exchange resin chelating with ferric ions. According to a preferred embodiment of the invention, there is provides the aforementioned method wherein the weakly basic anion exchange resin is a polyamine-type or an acrylic-type resin.

BEST MODE FOR CARRYING OUT THE INVENTION

Figure 1:
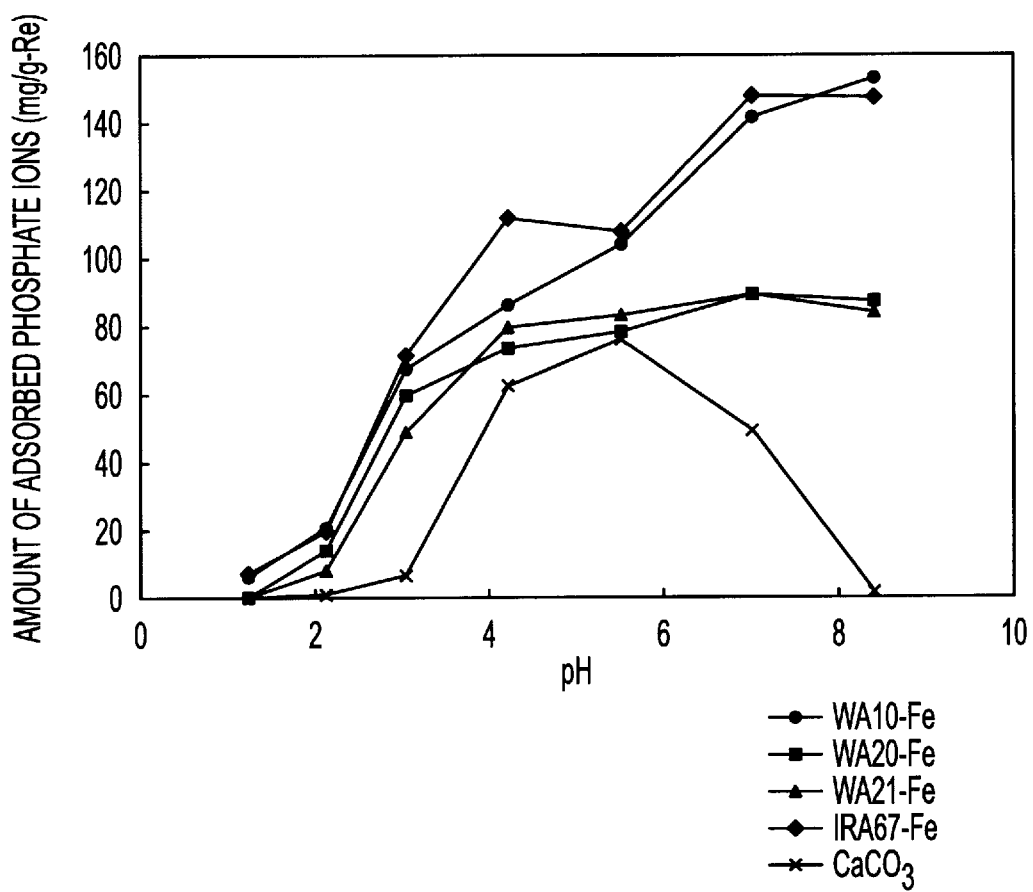
FIG. 1 shows pH-dependent changes in the amount of phosphate ions adsorbed by weakly basic anion exchange resins chelating with ferric ions (WA10-Fe, WA20-Fe, WA21-Fe, and IRA-67-Fe) and by precipitated calcium carbonate.

The present invention relates to a medicament which comprises as an active ingredient a weakly basic anion exchange resin chelating with ferric ions, preferably a polyamine-type or an acrylic-type weakly basic anion exchange resin, and is used for therapeutic and/or preventive treatment of hyperphosphatemia.

The weakly basic anion exchange resins used as a raw material for the manufacture of the medicaments of the present invention are not particularly limited so long as they can adsorb phosphate ions. Examples of preferred weakly basic anion exchange resins include polyamine-type resins (including polyamine-type chelating resins) such as reaction products of a styrene/divinylbenzene copolymer and diethylenetriamine or other, and resins as polymerization products of compounds mainly comprising allylamine, vinylamine or other; and acrylic resins such as copolymers of divinylbenzene and amide compounds which comprise acrylic acid or methacrylic acid and dimethylaminopropylamine or other. Other resins may also be used in which the aforementioned weakly basic anion exchange resin is partly substituted with strongly basic exchange groups such as trimethylamine, dimethylethanolamine or other.

More specifically, known resins which have been used so far for the treatment of water, sugar solutions and other can be used, for example, Diaion WA10, WNA20, WA21 and WA30 (Mitsubishi Chemical), Amberlite IRA-35, IRA-67 (IRA-68). IRA-93ZU, IRA-94S, IRA-478 (Organo). WGR-2 (Dow Chemical) and other.

The weakly basic anion exchange resins chelating with ferric ions, which are used as an active ingredient of the medicaments of the present invention, can be prepared as resins that are bound to (that adsorb) ferric ions and chloride ions (Cl form), for instance, by stirring the aforementioned weakly basic anion exchange resin in an aqueous solution containing metal salt such as ferric chloride, or alternatively, by charging a column with the resin, passing in aqueous solution containing metal salt such as ferric chloride through the column, and washing the column with water.

Additionally, the weakly basic anion exchange resin chelating with ferric ions can be prepared as resins that are bound to (that adsorb) ferric ions and hydroxide ions, or resins in which hydroxide ions are further dissociated from the resulting resins (OH form) by treating the resins obtained above (Cl form) with an alkaline solution such as a sodium hydroxide solution to eliminate the chloride ions, and then washing the resins with water.

When the weakly basic anion exchange resin chelating with ferric ions are manufactured according to the aforementioned methods, resins are normally obtained which contain about from 0.2 to 50 mg of iron per gram of a dry resin, although the content may vary depending on types of resins and other. However, the contents of iron in the weakly basic anion exchange resins are not limited to the aforementioned range, and the methods for preparing the weakly basic anion exchange resin chelating with ferric ions are not limited to the methods described above.

The medicament of the present invention comprises, as an active ingredient, the weakly basic anion exchange resin chelating with ferric ions, preferably the aforementioned resin in the OH form, or may comprise a combination of two or more of the aforementioned resins. As the medicaments of the present invention, the aforementioned resin prepared, for example, in spherical or crushed form, per se, may be administered to patients. Generally, the medicaments are preferably administered to patients in the form of pharmaceutical compositions which are prepared by using one or more pharmaceutical additives ordinarily used in the art. Pharmaceutical compositions in the form of powders, granules, tablets, capsules, for example, may be appropriately chosen. For example, after a composition containing a resin chelating with ferric ions (Cl form) is prepared, the composition may be applied with an enteric coating comprising hydroxypropyl methylcellulose phthalate, methacrylic copolymer L or other to use as a pharmaceutical composition.

Although not intended to be bound by any specific theory, a mechanism that the medicaments of the present invention exhibit phosphate eliminating effect in vivo can be explained as follows: after oral administration of the weakly basic anion exchange resin, the resin is converted into a form containing chloride ions in the stomach by the binding of chloride ions to nitrogen atoms in the resin (positively charged in gastric juice), or by the substitution of a part or all of hydroxyl groups bound ionically to the resin with chloride ions. After then, when the resin in this form reaches in the intestinal tract (weakly basic), the chloride ions are substituted with phosphate ions, and the phosphate ions in the intestinal tract are adsorbed to the resin. Simultaneously, the chloride ions substituted with the phosphate ions are returned to the body.

A reason that the weakly basic anion exchange resins chelating with ferric ions (especially those in the OH form), active ingredients of the medicaments of the present invention, are preferable may be explained as follows: the weakly basic anion exchange resin chelating with ferric ions has ligands of the iron site, and can efficiently adsorb phosphate ions also by the coordinate bonds. Additionally, because highly selective ferric ions are bound to the resin by chelation, the resin does not adsorb useful metal ions existing in the body (iron ion, zinc ion, calcium ion, magnesium ion and other), and can selectively eliminate only phosphate ions without substantially affecting the balance of electrolytes in vivo other than phosphate such as the balance of chloride ions. Furthermore, the medicaments of the present invention can selectively adsorb and eliminate only phosphate without substantially adsorbing bile acids including cholic acid, deoxycholic acid, and taurocholic acid.

The weakly basic anion exchange resins chelating with ferric ions sometimes desorbs the ferric ions to some extent in an artificial gastric juice: however, it has been verified that no ferric ions are desorbed from the resins in an artificial intestinal juice. Accordingly, it is considered that no desorption of ferric ion,s will arise when the medicament of the present invention becomes contact with the intestinal juice, and that almost no affection will be caused by the medicament. Moreover, ferric ions are not easily adsorbed in vivo and the irons per se are substantially non-toxic. Therefore, it can be considered that, even if a small amount of ferric ions are desorbed from the medicaments of the present invention, the medicaments will not adversely affect a living body. Nevertheless, to patients for whom an increase of iron ions is undesired, it is recommendable to administer a pharmaceutical composition obtained by applying an enteric coating on the resins in the Cl form in order to completely inhibit desorption of the ferric ions in the stomach.

The active ingredients of the medicaments of the present invention are quite stable chemically and can never be absorbed from the digestive tract. Therefore, there is almost no possibility that the medicament might cause adverse effects such as toxicity resulting from the resin, per se.

Types of hyperphosphatemia to which the medicaments of the present invention may be applied are not particularly limited. The medicaments can be applied to patients with renal dysfunction who need dialysis therapy, e.g., patients with chronic renal failure, for therapeutic and/or preventive treatment of hyperphosphatemia caused by the dialysis therapy. The dose of the medicaments of the present invention is not particularly limited. Generally, about from 1 to 100 g, preferably about from 5 to 30 g, per day an adult may be administered.

EXAMPLES

The present invention will be more specifically explained by referring to examples. However, the present invention is not limited to these examples.

Example 1

Preparation of Resins Chelating with Ferric Ions (a) To each 10 g of weakly basic anion exchange resins having a particle size of about from 400 to 600 μm (trade name: Diaion WA10, WA20, WA21 (Mitsubishi Chemical); IRA-67 (Organo)), 100 mL of a solution of 10% ferric chloride ($FeCl_3.6H_2O$) was added, and the resulting mixture was stirred for 24 hours. The anion exchange resins were separated by filtration, washed thoroughly with purified water, and dried at from 40 to 80° C. under seduced pressure to obtain resins adsorbing ferric ions and chloride ions (Cl form) [WA10-Fe, WA20-Fe, WA21-Fe, and IRA-67-Fe].

(b) Columns were charged with each resins obtained by a similar method to step (a) (resins before being dried under reduced pressure), and 70 mL of a 1 mol/L sodium hydroxide solution was passed through each column over about 1 to 2 days. Then, the resins were thoroughly washed with purified water and dried at from 40 to 80° C. under reduced pressure to obtain resins adsorbing ferric ions (OH form).

(c) The resins obtained in similar manners to step (b) were crushed to obtain crushed products having a particle size of 150 μm or less.

(d) Resins adsorbing ferric ions (OH form) were obtained in similar manners to steps (a) and (b), except that resins were used after having been crushed beforehand so as to have a particle size of 150 μm or less.

Example 2

Preparation of a Pharmaceutical Composition Applied with an Enteric Coating

A weakly basic anion exchange resin chelating with ferric ions (obtained by a similar manner to step (a) in Example 1: WA20-Fe) (150 g) was fluidized in a fluidized bed-coating machine (Unigratt, Ohkawara Seisakusho), and then coated by using 500 g of the following coating solution under the conditions described below to obtain a resin applied with an enteric coating (WA20-Fe—C). The resulting resin was found to have the coating amount of 8%.

(a) Coating solution: Hhydroxypropyl methylcellulose phthalate (30 g, HP50, Shinetsu Kagaku) was dispersed in 510 g of ethanol. Then, 60 g of purified water was added to the mixture to obtain a coating solution.

(b) Coating conditions:

| | |
|---|---|
| Inlet air temperature | 35° C. |
| Outlet air temperature | 25° C. |
| Spraying pressure | 2.5 kg/cm³ |
| Flow rate of the coating solution | 4.8 g/min |

Example 3

Adsorbability of Phosphate Ions by the Medicaments of the Present Invention

A resin chelating with ferric ions [0.05 g. prepared by the same manner as step (a) in Example 1: WA10-Fe. WA-20-Fe, WA21-Fe or IRA-67-Fe] or precipitated calcium carbonate ($CaCO_3$) was added to 100 ml, of a 0.02% disodium phosphate solution, whose pH were adjusted beforehand to about 2 to 8 with a solution of sodium hydroxide or hydrochloric acid. Each mixture was stirred at 37° C. for 1 hour and filtered, and the phosphate ion ($PO_4^{-3}$) in the filtrate was determined by the phosphorus molybdenum blue method. The results are shown in FIG. 1.

As shown in FIG. 1, the resins chelating with ferric ions, i.e., WA10-Fe, WA20-Fe, WA21-Fe and IRA-670-Fe, excellently adsorbed phosphate ions at pH 4 or higher (neutral to weakly alkaline conditions). Accordingly, all of the resins are expected to have a phosphate eliminating effect in the intestinal tract. Moreover, these resins had almost the same or higher phosphate adsorbability compared to precipitated calcium carbonate which has been used as a primary drug for the treatment of hyperphosphatemia.

Example 4

Desorption of Ferric Ions from the Medicaments of the Present Invention

Weakly basic anion exchange resins chelating with ferric ions (Cl form) [0.25 g, prepared by the same manner as step (a) in Example 1: WA10-Fe, WA20-Fe, WA21-Fe and IRA-67-Fe] was added to 25 mL of the first solution (artificial gastric juice, pH 1.2) or the second solution (artificial intestinal juice, pH 6.8) described in the disintegration test of the 13th revised edition of the Japanese Pharmacopoeia. The resulting mixtures were stirred at 37° C. for 2 hours and filtered, and the iron contents in the filtrates were determined. The results are shown in Table 1.

(a) Preparation of the first solution: Hydrochloric acid (7 mL) and water were added to 2.0 g of sodium chloride to obtain 1,000 mL of a colorless, transparent solution having the pH of about 1.2.

(b) Preparation of the second solution: 118 mL of a 0.2 mol/l sodium hydroxide solution and water were added to 250 mL of a 0.2 mol/l potassium dihydrogenphosphate solution to obtain 1,000 mL of a colorless, transparent solution having the pH of about 6.8.

TABLE 1

| Resin | Iron content of resin (mg/g, dry) | Iron desorption (mg/g, dry) | |
|---|---|---|---|
| | | First solution | Second solution |
| WA10-Fe | 28.9 | 3.0 | 0.0 |
| WA20-Fe | 28.5 | 0.8 | 0.0 |
| WA21-Fe | 2.2 | 0.3 | 0.0 |
| WA21-Fe* | 1.9 | 0.3 | 0.0 |

TABLE 1-continued

| Resin | Iron content of resin (mg/g, dry) | Iron desorption (mg/g, dry) | |
|---|---|---|---|
| | | First solution | Second solution |
| WA21-Fe** | 0.5 | 0.2 | 0.0 |
| IRA-67-Fe | 13.5 | 3.7 | 0.0 |

*adsorbed with iron, and then crushed into 150 μm or less.
**crushed into 150 μm or less, and then adsorbed with iron.

As readily understood from the results shown in Table 1, the weakly basic anion exchange resins chelating with ferric ions contained about from 0.5 to 30 mg of iron per gram of the resin in a dried state, although the ferric ion contents were slightly changed depending on differences in degrees of cross-linking, forms (porous, high porous, gel form), or the state of crushing and other, even though the resins had exchange groups of the same chemical structure.

The weakly basic anion exchange resins chelating with ferric ions desorbed a part of the chelated ferric ions in the first solution, and the ratios were slightly different depending on types of the resins. On the other hand, no desorption of the ferric ions in the second solution was observed in any of the resins. By using WA21, changes in iron desorbing ratios were studied which were caused by differences in the treatment of crushing and other. As a result, some changes were observed. The phosphate ion adsorbability of the crushed resin was almost the same or slightly higher compared to the non-crushed resin.

Example 5

Adsorption of Metal Ions to the Medicaments of the Present Invention

To each 100 mL or 0.2 M solutions (stock solutions) of ferrous chloride ($FeCl_3$), zinc chloride ($ZnCl_2$), magnesium chloride ($MgCl_2$) and calcium chloride ($CaCl_2$), 1 g of a sample (resins prepared in the same manner as step (a) in Example 1: WA10-Fe or IRA-67-Fe, or cholestyramine which has bile acid-adsorbing action and is known as a cholesterol depressant) was added, and the resulting mixtures were stirred at room temperature for 1 hour and then filtered. The filtrates and the stock solutions were subjected to capillary electrophoresis to determine the ions of $Fe^{+2}$. $Zr^{+2}$. and $Ca^{+2}$, and adsorbed amounts of the metal ions to each resins were calculated from a difference of an ionic concentration between the filtrate and the stock solution. The results are shown in Table 2. From the results shown in Table 2, it is apparent that the weakly basic anion exchange resins chelating with ferric ions exhibit no adsorption of any of the ions.

| Determination conditions for capillary electrophoresis | |
|---|---|
| Apparatus: | Hewlett-Packard, 3D CE |
| Column: | Fused Silica (75 μm in diameter, 53 cm in height) |
| Buffered solution: | Mixture of 10 mM imidazole and 5 mM lactic acid, pH 4.5 (adjusted with 1M acetic acid) |
| Injection method: | Pressuring procedure, 2.5 sec at 50 mbar |
| Voltage: | +20 kV |
| Detector: | Photodiode array Signals 280 nm Reference 210 nm |

TABLE 2

| Adsorbent | $Ca^{+2}$ | $Mg^{+2}$ | $Zn^{+2}$ | $Fe^{+2}$ |
|---|---|---|---|---|
| WA10-Fe | 0.0 | 0.0 | 0.0 | 0.0 |
| IRA-67-Fe | 0.0 | 0.0 | 0.0 | 0.0 |
| Cholestyramine | 0.0 | 0.0 | 0.0 | 0.1 mg/g |

Example 6

Adsorption of Bile Acids to the Medicaments of the Present Invention

WA10-Fe and IRA-67-Fe prepared by the method of step (a) and step (b) in Example 1 were used as test samples, and cholestyramine was used as a control. A mixture containing equal volume of 2 mg/ml suspension of the sample and a 5 mM aqueous solution of a bile acid was stirred at 37° C. for 1 hour. The bile acid adsorbed to the sample was desorbed by filtration by using chromatographic disc (0.45 μm), and the amount of the bile acid adsorbed by the sample was determined on the basis of the amount of the bile acid in the filtrate. The measurement of the bile acid was carried out according to the enzyme method using Enzabile 2 (Daiichi Pure Chemicals, Co., Ltd.). The results are shown in Table 3.

TABLE 3

| | Adsorbed amount (mM/g-R, dry) | | | | |
|---|---|---|---|---|---|
| | WA10-Fe | | IRA-67-Fe | | Choles- |
| Bile acid | Cl form | OH form | Cl form | OH form | tyramine |
| Cholic acid | 0.0 | 0.0 | 0.0 | 0.0 | 3.0 |
| Deoxycholic acid | 0.0 | 0.0 | 0.0 | 0.0 | 5.3 |
| Tarocholic acid | 0.0 | 0.0 | 0.0 | 0.0 | 5.3 |
| Glycocholic acid | 0.0 | 0.0 | 0.0 | 0.0 | 4.5 |

As shown in Table 3, cholestyramine as a cholesterol lowering agent adsorbed bile acids, whereas the weakly basic anion exchange resins chelating with ferric ions exhibited no adsorption of bile acids.

Example 7

Effect of the Medicaments of the Present Invention on Rats (a) S.D. male rats (7-week old, Japan Charles River) were used as experimental animals. The animals were preliminarily bred under restricted feeding with 20 g/rat of normal powdery feed CE-2 (Nippon Crea) in a metabolic cage at a constant temperature of 25±5° C. and a constant humidity of 55 ±10% for 1 week, and then subjected to the test. The preliminarily bred rats were divided into groups of 5 rats on the basis of body weight, and bred for 7 days under restricted feeding with 80 g/kg/day of the normal powdery feed supplemented with 10% of WA20, a weakly basic anion exchange resin; WA20-Fe, the resin further chelated with ferric ions in a similar manner to step (a) in Example 1; or WA20-Fe—C, the above-obtained resin further applied with an enteric coating. The amount of urinary phosphate (one day amount) excreted in day 7 and the amount of fecal phosphate (7 days amount) excreted during the administration period were determined. In a similar manner, the amount of phosphate in the group fed solely with the normal powdery feed (control) was determined.

The urinary phosphate (inorganic phosphate) was determined by using an autoanalyzer (COBAS PARA). The fecal phosphate was determined by drying fecal bulks, and then decomposing organic substances by wet oxidation using a semi-micro-Kjeldahl apparatus, and determining phosphate ions by the phosphorus molybdenum blue method. The results are shown in Table 4 (effect on urinary phosphate) and Table 5 (effect on fecal phosphate).

TABLE 4

| Group | Urinary phosphate (mg/rat/day) |
|---|---|
| Control | 24.58 ± 1.56 |
| WA20-Fe administered | 11.86 ± 1.59** |
| WA20-Fe—C administered | 13.14 ± 2.04** | n = 5;
**$p < 0.01$ (significant difference compared to the control in the t-test)

TABLE 5

| Group | Fecal phosphate (mg/rat/weak) |
|---|---|
| Control | 0.57 ± 0.03 |
| WA20-Fe administered | 0.72 ± 0.01** |
| WA20-Fe—C administered | 0.70 ± 0.01** | n = 5;
**$p < 0.01$ (significant difference compared to the control in the t-test)

(b) Phosphate adsorbability was examined in a similar manner to the aforementioned test using WA10-Fe, WA20-Fe and WA21-Fe, which were crushed products in the OH form prepared according to a method similar to step (d) in Example 1 by using WA10, WA20 and WA21 as the weakly basic anion exchange resins, and precipitated calcium carbonate. The results are shown in Table 6 (effect of each resins on urinary phosphate) and Table 7 (effect of each resins on fecal phosphate).

TABLE 6

| Group | Urinary phosphate (mg/rat/day) |
|---|---|
| Control | 23.78 ± 1.47 |
| WA10-Fe administered | 0.12 ± 0.02** |
| WA20-Fe administered | 8.08 ± 1.10** |
| WA21-Fe administered | 2.00 ± 0.61** |
| $CaCO_3$ administered | 0.06 ± 0.02** | n = 5;
**$p < 0.01$ (significant difference compared to the control in the t-test)

TABLE 7

| Group | Fecal phosphate (mg/rat/weak) |
|---|---|
| Control | 0.84 ± 0.01 |
| WA10-Fe administered | 1.06 ± 0.06** |
| WA20-Fe administered | 1.01 ± 0.03** |
| WA21-Fe administered | 0.99 ± 0.02** |
| $CaCO_3$ administered | 1.03 ± 0.09** | n = 5;
**$p < 0.01$ (significant difference compared to the control in the t-test)

From the results shown in Table 4 and Table 5, it can be understood that WA20-Fe which was obtained by chelating WA20 as a weakly basic anion exchange resin with ferric ions, and a resin applied with an enteric coating in Example 2 (WA20-Fe—C) significantly reduced urinary phosphate compared to the controls, and also significantly increased fecal phosphate. Accordingly, these resins were verified to have phosphate eliminating effects in the digestive tract. The resin applied with an enteric coating (WA20-Fe—C) gave results almost equal to those of the other resins, and this resin was also verified to have adsorbability of phosphate ions in the intestinal tract.

In addition, as apparent from the results shown in Table 6 and Table 7, urinary excreted phosphates were significantly reduced and fecal excreted phosphates were significantly increased in the groups administered with WA10-Fe, WA20-Fe and WA21-Fe, which were obtained by crushing WA10, WA20 and WA21 as the weakly basic anion exchange resins, and then carrying out chelation with ferric ions, and in the group administered with precipitated calcium carbonate, as compared to control group. Accordingly, these resins were also verified to have a phosphate eliminating effect in vivo.

Although these resins have the exchange groups of the same chemical structure, they exhibited slightly different phosphate adsorbability. The result may be elucidated that the resins had differences in their cross-linking ratios, forms and other. Among these resins, WA10-Fe exhibited almost the same phosphate eliminating ability as that of precipitated calcium carbonate, and this resin was verified to have excellent phosphate eliminating effect.

Example 8

Effect of Medicaments of the Present Invention on Adenine-induced Chronic Renal Failure in Rats (a) S.D. male rats (6-week old, Japan Charles River) vore used as experimental animals. The animals were preliminarily bred under restricted feeding with 20 g/rat of normal powdery feed CE-2 in a metabolic cage at a constant temperature of 25±5° C. and a constant humidity of 55±10%, for 1 week, and the rats were divided into groups of 6 to 8 rats on the basis of body weight and subjected to the tests. The experiments were carried out by measuring blood phosphate concentrations of the following groups: a group fed with CE-2 containing 0.5% adeniine for 4 weeks (control); and a group fed for 4 weeks with the aforementioned 0.5% adenine containing CE-2 added with 10% WA10-Fe or WA21-Fe, which were crushed products of weakly basic anion exchange resins in the OH form obtained by a similar manner to step (c) in Example 1. At the starting day of the test and after feeding for 4 weeks, the blood was collected from their caudal veins and the blood phosphate concentration (inorganic phosphate concentration) was measured by using an autoanalyzer (EKTACHEM KODAK). Similar tests were performed using precipitated calcium carbonate to compare the effects. The results are shown in Table 8.

TABLE 8

| Group | Number of rat | Blood phosphate concentration (mg/dL) |
|---|---|---|
| Control (before the test) | 8 | 6.38 ± 0.19 |
| Control | 8 | 12.03 ± 0.70 |
| WA10-Fe administered | 6 | 4.83 ± 1.06** |
| WA21-Fe administered | 6 | 8.17 ± 1.28* |
| $CaCO_3$ administered | 6 | 3.43 ± 0.14** |

*$p < 0.05$,
**$p < 0.01$ (significant difference compared to the control in the t-test)

As shown in Table 8, the blood phosphate concentration was almost doubled by feeding rats with the adenine-containing feed for 4 weeks compared to the concentration at the starting day, which indicates establishment of rats suffering from chronic renal failure with hyperphosphatemia. In contrast, the groups fed with the feed admixed with WA10-Fe and WA21-Fe, which are weakly basic anion exchange resins chelating with ferric ions, and precipitated calcium carbonate exhibited significant decreases in blood phosphate concentration compared to the control.

(b) S.D. male rats (6-week old, Japan Charles River) were preliminary bred under restricted feeding with 20 g/rat of CE-2 in a metabolic cage at a constant temperature of 25±5° C. and a constant humidity of 55±10% for 1 week. Then, the rats were fed with CE-2 containing 0.5% adenine for 4 weeks to prepare rats suffering from renal failure. Separately, another group was fed with CE-2 for 4 weeks to prepare a group of non-renal failure rats (normal group). The rats suffering from renal failure were divided into groups of from 4 to 7 rats on the basis of blood phosphate concentrations measured in the third week of feeding the adenine-containing feed, and subjected to the test.

Experiments were carried out by measuring blood phosphate concentration of the following groups: a group fed with CE-2 for 1 week (control group), and groups fed for 1 week with CE-2 supplemented with 5% WA10-Fe, which was crushed product of a weakly basic anion exchange resin in the OH form obtained in a similar manner to step (d) in Example 1, or with 5% IRA-67-Fe, which was crushed product of a weakly basic anion exchange resin in the OH form obtained in a similar manner to step (b) in Example 1. The normal group was fed with CE-2 for 1 week and subjected to the same treatments. The blood was collected from the caudal veins in the third week of feeding the adenine-containing feed and on the last day of the test. Similar tests were also performed using precipitated calcium carbonate to compare the effects. The results are shown in Tables 9 and 10.

TABLE 9

| Group | Number of rat | Blood phosphate concentration (mg/dL) |
| --- | --- | --- |
| Normal | 7 | 5.21 ± 0.25 |
| Control | 7 | 7.51 ± 0.19 |
| WA10-Fe | 6 | 3.52 ± 0.73** |
| CaCO$_3$ | 6 | 1.13 ± 0.14** |

**$p < 0.01$ (significant difference compared to the control in the t-test)

TABLE 10

| Group | Number of rat | Blood phosphate concentration (mg/dL) |
| --- | --- | --- |
| Normal | 6 | 5.58 ± 0.21 |
| Control | 5 | 9.08 ± 0.35 |
| IRA-67-Fe | 4 | 5.55 ± 0.39** |

**$p < 0.01$ (significant difference compared to the control in the t-test)

As shown in Tables 9 and 10, a significant increase in the blood phosphate concentration (1% significant difference in the t-test) was observed, as compared to the normal group, in rats fed with the adenine-containing feed for 4 weeks to generate chronic renal failure and then with the normal feed for 1 week (control group), even after the onset of chronic renal failure. In contrast, the blood phosphate concentration was significantly decreased, as compared to the control, in the groups fed with feeds admixed with WA10-Fe or IRA-67-Fe, which were weakly basic anion exchange resins, or precipitated calcium carbonate for 1 week after the onset of chronic renal failure.

From these results, it was revealed that the medicaments of the present invention which comprise a weakly basic anion exchange resin chelating with ferric ions can exert effectiveness on hyperphosphatemia in renal failure by administrations in a progressive stage to onset or after the onset.

Industrial Applicability

The medicaments of the present invention have excellent adsorbability and selectivity to phosphate ions and efficiently adsorb phosphate ions in vivo, and accordingly, they are useful for therapeutic and/or preventive treatment of hyperphosphatemia. The medicaments or the present invention also have an excellent characteristic of no adsorption of ions other than phosphate ions, and they enable effective therapeutic and/or preventive treatment of hyperphosphatemia without affecting the balance of essential metal ions to the body.

What is claimed is:

1. A medicament which comprises a weakly basic anion exchange resin chelating with ferric ions as an active ingredient, the weakly basic anion exchange resin comprising an acrylic resin of a copolymer of divinylbenzene and an N-(ω-dimethylaminoalkyl)amide compound.

2. The medicament of claim 1, wherein the resin comprises from about 0.2 to about 50 mg of iron per gram of the resin.

3. The medicament of claim 1, wherein the resin is in the OH form.

4. The medicament of claim 1, wherein the resin is in the Cl form.

5. A method of treating hyperphosphatemia in a patient in need of such treatment, comprising administering to said patient a therapeutically effective amount of at least one weakly basic anion exchange resin chelating with ferric ions, the weakly basic anion exchange resin comprising an acrylic resin of a copolymer of divinylbenzene and an N-(ω-dimethylaminoalkyl)amide compound.

6. The method of claim 5, wherein the hyperphosphatemia is caused by dialysis therapy.

7. The method of claim 5, wherein from about 1 to about 100 g of weakly basic anion exchange resin chelating with ferric ions are administered per day.

8. The method of claim 7, wherein from about 5 to about 30 g of weakly basic anion exchange resin chelating with ferric ions are administered per day.

9. The method of claim 5, wherein the resin comprises from about 0.2 to about 50 mg of iron per gram of the resin.

10. The method of claim 9, wherein the resin is in the OH form.

11. The method of claim 9, wherein the resin is in the Cl form.

12. A method of preventing hyperphosphatemia in a patient in need of such treatment, comprising administering to said patient an effective amount of at least one weakly basic anion exchange resin chelating with ferric ions, the weakly basic anion exchange resin comprising an acrylic resin of a copolymer of divinylbenzene and an N-(ω-dimethylaminoalkyl)amide compound.

13. The method of claim 12, wherein the hyperphosphatemia is caused by dialysis therapy.

14. The method of claim 13, wherein from about 1 to about 100 g of weakly basic anion exchange resin chelating with ferric ions are administered per day.

15. The method of claim 14, wherein from about 5 to about 30 g of weakly basic anion exchange resin chelating with ferric ions are administered per day.

16. The method of claim 15, wherein the resin comprises from about 0.2 to about 50 mg of iron per gram of the resin.

17. The method of claim 16, wherein the resin is in the OH form.

18. The method of claim 16, wherein the resin is in the Cl form.

* * * * *